United States Patent [19]
Huang

[11] Patent Number: 5,869,275
[45] Date of Patent: Feb. 9, 1999

[54] AFFINITY ULTRAFILTRATION ASSAY FOR TRANSFERASE ACTIVITY

[76] Inventor: Eric Z. Huang, 1419-J Winter Park Cir., Baltimore, Md. 21221

[21] Appl. No.: 118,900

[22] Filed: Jul. 20, 1998

[51] Int. Cl.$^6$ .............................. C12Q 1/48; C12Q 1/37; G01N 33/53

[52] U.S. Cl. .............................. 435/15; 435/7.5; 435/7.4; 435/7.1; 435/975; 435/24; 435/4; 435/968

[58] Field of Search ................................. 435/15, 7.5, 7.4, 435/968, 7.1, 4, 975, 24

[56] References Cited

U.S. PATENT DOCUMENTS

| | | | |
|---|---|---|---|
| 4,973,554 | 11/1990 | Luong et al. | 435/213 |
| 5,034,314 | 7/1991 | Geiger et al. | 435/6 |
| 5,141,851 | 8/1992 | Brown et al. | 435/15 |
| 5,141,852 | 8/1992 | Egan et al. | 435/15 |
| 5,527,688 | 6/1996 | Mallia | 435/15 |
| 5,538,858 | 7/1996 | Mallia | 435/15 |
| 5,580,747 | 12/1996 | Schultz et al. | 435/24 |

OTHER PUBLICATIONS

Life Technologies Technical Bulletin, "Protein Kinase C Assay" (1995).
NEN™ Life Science Products Technical Bulletin, "Use of Flash Plate® for Chloramphenicol Acetyl Transferase Assay" (1996).
Promega Technical Bulletin, "SignaTECT™ Protein Tyrosine Kinase Assay System" (1996).
Calbiochem® Technical Bulletin, "Non–Radioactive Protein Kinase Assay Kit" (1996).
Amicon® Technical Bulletin, "Microcon® Microconcentrators" (1996).
Jerini Technical Bulletin, "Characterize Your Kinases" (1998).
Amersham Technical Bulletin, "Drug Development Services" (1998).
Cook, et al., "Adenosine Cyclic 3',5'–Monophosphate Dependent Protein Kinase: Kinetic Mechanism for the Bovine Skeletal Muscle Catalyst Subunit", *Biochemistry 21*: 5794–5799 (1982).
Sleigh, "A Nonchromomatographic Assay for Expression of the Chloramphenicol Acetyltransferase Gene in Eucaryotic Cells", *Analytical Biochemistry 156*: 251–256 (1986).
Platt, et al., "Dot Assay for Neomycin Phosphotransferase Activity in Crude Cell Extracts", *Analytical Biochemistry 162*: 529–535 (1987).
Cabanes–Bastos, et al., "A Sensitive and Simple Assay for Neomycin Phosphotransferase II Activity in Transgenic Tissue", *Gene 77*: 169–176 (1989).
McIlroy, et al., "A Continuous Fluorescence Assay for Protein Kinase C", *Analytical Biochemistry 195*: 148–152 (1991).
Borrowman, et al., "An Improved Washing Apparatus for Nucleoside Phosphorylation Assays", *BioTechniques 15*: 402–406 (1993).
Lefevre, et al., "Quantitative Nonradioactive CAT Assays Using Fluorescent BODIPY® 1–Deoxychloramphenicol Substrates", *BioTechniques 19*: 488–493 (1995).

*Primary Examiner*—Louise N. Leary

[57] ABSTRACT

The present invention relates to a method for assaying transferase activity upon incorporation of an affinity ultrafiltration process as a separation means, which method comprises: (1) reacting the transferase to be assayed with a labeled substrate and an unlabeled substrate to yield a product having a label moiety from the labeled substrate and a binding site moiety either from the unlabeled substrate or existing as a specific structure of the product, (2) contacting the reaction mixture with a soluble macroligand capable of forming a specific complex with the product via the binding site moiety, (3) subjecting the complex mixture to ultrafiltration which retains the complex and passes the unreacted labeled substrate, (4) washing the retentate, and (5) determining the final retentate. The present invention also relates to a kit embodying the inventive concept of the affinity ultrafiltration assay for transferase activity.

29 Claims, No Drawings

AFFINITY ULTRAFILTRATION ASSAY FOR TRANSFERASE ACTIVITY

FIELD OF THE INVENTION

The present invention relates to a method for assaying transferase activity which incorporates an affinity ultrafiltration process as a separation means.

DESCRIPTION OF THE PRIOR ART

Transferase in this invention refers to a type of enzyme which catalyzes transfer of at least part of one compound to at least part of another compound. Specific examples of transferase include, but are not limited to, protein kinase, farnesyl transferase, thymidine kinase, chloramphenicol acetyltransferase, and neomycin phosphotransferase. Assay of activity of protein kinase or farnesyl transferase is of significance in biological and pharmaceutical research due to the roles these enzymes play in the molecular communications of the living systems. Activity of thymidine kinase in serum is measured for its correlation with breast cancer stage. On the other hand, determination of activity of chloramphenicol acetyltransferase or neomycin phosphotransferase to report gene expression is a standard laboratory technique.

To assay activity of a transferase sample, the enzyme sample is reacted with a substrate and buffer system to yield a product. A detection system which recognizes and quantifies the product is then in use to give a measure of the transferase activity. The prior art concerning the methods for assaying activities of the common transferases is detailed herein below.

Protein Kinase

Protein kinase catalyzes transfer of gamma phosphate from adenosine triphosphate (ATP) to a tyrosine, serine, threonine or histidine residue in a peptide or protein molecule. Use of a short peptide substrate with a defined sequence of amino acid for assaying protein kinase activity is a common technique as it yields the desired specificity or classification for the protein kinase sample being assayed.

In one method for assaying protein kinase activity, ADP formed in the kinase reaction is utilized to convert phosphoenolpyruvate to pyruvate in the presence of pyruvate kinase. The pyruvate thus formed is further converted to lactate by lactate dehydrogenase and detected by reading the absorbance at 340 nm (Biochemistry 21: 5794–5799, 1982). While effective, this method is not very sensitive, and is subject to interference of ATP hydrolase activity in a crude sample which also generates ADP independent of the protein kinase activity of assay interest.

In another method for assaying protein kinase activity, the kinase sample is in contact with an immobilized peptide substrate in the presence of ATP. The phosphorylation of the immobilized peptide as an indicator of the kinase activity is measured via binding of an antibody specific to the phosphorylated peptide product followed by an enzymatic detection (Calbiochem® Technical Bulletin, Non-Radioactive Protein Kinase Assay Kit, 1996). The main drawbacks of this method include the kinetic complications of the enzymatic reaction on the solid phase, and the time and reagent expenses associated with the antibody detection steps.

The peptide phosphorylation catalyzed by a protein kinase in the presence of ATP may also be reported by a change in the fluorescent signal of a phosphorylation sensitive dye attached to the peptide substrate (Analytical Biochemistry 195: 148–152, 1991). While such signal change fulfills direct assay for the protein kinase activity without separation, this assay method has low sensitivity due to the considerable background of the fluorescent peptide substrate itself.

Other approaches for protein kinase activity assay are commenced by reacting the kinase sample with either a mixture of gamma $^{32}$P-ATP and an unlabeled peptide substrate, or a mixture of cold ATP and a labeled peptide substrate. The protein kinase activity is detected after the labeled and phosphorylated peptide product is separated from the unreacted gamma $^{-}$P-ATP or the unreacted labeled peptide substrate.

The first method group for assaying protein kinase activity based on the labeling and separation approach are developed by exploiting the reaction of the protein kinase sample with gamma $^{32}$P-ATP and an unlabeled peptide substrate. One method makes use of the preferential binding of the $^{32}$P-peptide product to a phosphocellulose membrane over gamma $^{32}$P-ATP (Life Technologies Technical Bulletin, Protein Kinase C Assay, 1995). In order to firmly bind to the phosphocellulose membrane the peptide substrate or product must contain a substantial fraction of basic amino acid residues, imposing a limitation on the choice of the peptide substrate sequence for assay specificity and optimization. The second drawback, which is inherent to the solid phase (phosphocellulose membrane in this case) binding and separation process, is the inconvenient manual handling and the generation of a large quantity of liquid radioactive waste. To overcome the limitation on the peptide substrate sequence, an improvement is made which achieves consistent separation of the $^{32}$P-peptide product from gamma $^{32}$P-ATP by tagging the peptide substrate with biotin and binding of the biotinylated $^{32}$P-peptide product to a streptavidin membrane (Promega Technical Bulletin, SignaTECT™ Protein Tyrosine Kinase Assay System, 1996). The peptide substrate can even be immobilized to a solid support for a reaction with a protein kinase sample in the presence of gamma $^{32}$P-ATP and easy separation of the $^{32}$P-peptide product from gamma $^{32}$P-ATP for measuring the kinase activity (Jerini Technical Bulletin, Characterize Your Kinases, 1998). Unfortunately, these two solid phase separation strategies do not solve the problems of the inconvenient solid phase handling and the excessive radioactive waste. A centrifugal chamber having a phosphocellulose membrane installed inside is designed as a compact and contained system for separating the $^{32}$P-peptide product from gamma $^{32}$P-ATP (U.S. Pat. No. 5,538,858). This design eases the solid phase handling and reduces the radioactive waste. However, the difficulty in quantitatively recovering the bound $^{32}$P-peptide product from the phosphocellulose membrane inside the chamber leads to the use of the whole chamber for radioactive counting, reducing the counting efficiency and reproducibility particularly when one of the low-energy labels such as $^{3}$H, $^{14}$C, $^{35}$S, and $^{33}$P is used. Separation of the $^{32}$P-peptide product from gamma $^{32}$P-ATP can also be done using tandem columns of cation and anion exchange resins (U.S. Pat. No. 5,141,852). It is obvious that this separation technique is too time consuming for a large number of samples, and lacks the appeal for commercialization.

The second method group for assaying protein kinase activity based on the labeling and separation approach are derived from the reaction of the protein kinase sample with cold ATP and a labeled peptide substrate. One method takes advantage of the higher affinity of the labeled and phosphorylated peptide product to a Fe$^{3+}$ containing membrane than the labeled peptide substrate (U.S. Pat. No. 5,527,688).

Certain peptide substrates, particularly those having acidic amino acid residues, may also bind to the $Fe^{3+}$ membrane through the charge interactions. This labeled substrate binding results in high background and therefore low sensitivity for the $Fe^{3+}$ membrane based protein kinase activity assay. Another method uses electrophoresis to separate the labeled and phosphorylated peptide product from the labeled peptide substrate by virtue of the increased negative charges upon the phosphorylation (U.S. Pat. No. 5,580,747). This assay procedure is cumbersome, and can be a bottleneck for a continuous work flow.

Farnesyl Transferase

Farnesyl transferase catalyzes transfer of a farnesyl group from farnesyl pyrophosphate (FPP) to a cysteine residue in a peptide or protein molecule. For sequence based specificity and classification of the farnesyl transferase activity being assayed, a synthetic short peptide is often used as a substrate for the assay reaction.

Assay for farnesyl transferase activity relies on differentiation of the labeled and farnesylated peptide product from the unreacted $^3H$ or $^{14}C$ labeled FPP after the transferase sample is reacted with the labeled FPP and a peptide substrate. One differentiation assay method is based separation by thin layer chromatography, or by tagging of the peptide substrate with biotin and binding of the biotinylated, farnesylated and labeled peptide product to a streptavidin resin (U.S. Pat. No. 5,141,851). The thin layer chromatography separation method is undesirable for a continuous work flow, while the streptavidin resin based separation is inconvenient to perform and incurs a considerable amount of liquid radioactive waste.

Another differentiation assay method is made possible using the scintillation proximity phenomenon. In this method, a biotinylated peptide substrate is labeled after accepting a $^3H$ labeled farnesyl group from $^3H$-FPP upon the action of farnesyl transferase activity in a sample being assayed. The reaction mixture is then incubated with a bead coated with streptavidin and a scintillant. The biotinylated, farnesylated and $^3H$ labeled peptide product binds to streptavidin on the bead and gives scintillation because of its proximity to the scintillant, while the unreacted free $^3H$-FPP in the solution gives no scintillation as its radiation energy decays in the bulky aqueous phase before reaching the scintillant. The result is homogeneous assay for farnesyl transferase activity (Amersham Technical Bulletin, Drug Developement Services, 1998). The main problem of this assay method is the relatively high cost of the streptavidin scintillant bead.

Thymidine Kinase

Thymidine kinase catalyzes transfer of gamma phosphate from ATP to thymidine. A typical protocol for assaying thymidine kinase activity begins with a reaction of the enzyme with $^3H$-thymidine and ATP. The $^3H$ labeled and phosphorylated thymidine as a product, and a measure, of the enzymatic activity is detected after it binds to a cationic membrane and is separated from the unreacted $^3H$-thymidine (BioTechniques 15: 402–406, 1993). This assay method again uses a solid phase for separation, and therefore is inconvenient to perform and generates excessive radioactive waste. Further, the assay concept excludes gamma $^{32}P$-ATP as a labeled substrate due to the background binding of the labeled ATP to the cationic membrane.

Chloramphenicol Acetyltransferase

Chloramphenicol acetyltransferase catalyzes transfer of an acetyl group from acetyl CoA to chlorampheniccol. To assay activity of this transferase, the enzyme is reacted with one labeled substrate and another unlabeled substrate to produce a labeled product. The transferase activity is determined upon differentiation of the labeled product from the unreacted labeled substrate.

One widely used method for assaying chloramphenicol acetyltransferase activity relies on thin layer chromatography separation (BioTechniques 19: 488–493, 1995). Like any other chromatographic assay method, this one has a low throughput. Another assay method contains a step of organic solvent extraction to separate the labeled product from $^{14}C$-acetyl CoA as a labeled substrate (Analytical Biochemistry 156: 251–256, 1986). Such solvent extraction technique is obviously undesirable for a routine laboratory operation.

The third method for assaying chloramphenicol acetyltransferase activity is designed for operational ease. In this method, biotinylated chloramphenicol is immobilized on a microtiter plate coated with streptavidin and a scintillant. Chloramphenicol acetyltransferase transfers a $^3H$ or $^{14}C$ labeled acetyl group from the labeled acetyl CoA to the immobilized chloramphenicol. The labeled chloramphenicol as the reaction product on the plate's surface promotes scintillation from the plate to indicate the transferease activity, while the radiation energy of the unreacted labeled acetyl CoA is absorbed in the aqueous medium and produces no appreciable scintillation background (NEN™ Life Science Products Technical Bulletin, Use of FlashPlate® for Chloramphenicol Acetyl Transferase Assay, 1996). This separation free assay is achieved, however, at a high cost associated with the use of the streptavidin and scintillant coated microtiter plate and a specialized microtiter plate counter.

Neomycin Phosphotransferase

Neomycin phosphotransferase catalyzes transfer of gamma phosphate from ATP to neomycin. Activity assay for this transferase is usually done with a reaction of the enzyme with gamma $^{32}P$-ATP and neomycin and separation of $^{32}P$-neomycin as the reaction product from the unreacted gamma $^{32}P$-ATP. One method for assaying neomycin phosphotransferase activity uses thin layer chromatography to separate the $^{32}P$-neomycin product from gamma $^{32}P$-ATP (Gene 77: 169–176, 1989). This chromatographic technique does not provide a high throughput. Another assay method is dependent on binding of the $^{32}P$-neomycin product to a phosphocellulose membrane (Analytical Biochemistry 162: 529–535, 1987). Again, this solid phase separation technique is associated with the inconvenient handling and the excessive radioactive waste.

Affinity Ultrafiltration Separation

In an independent development, affinity ultrafiltration which combines affinity binding and ultrafiltration has emerged as a novel separation process of industrial scale. In the first step, a soluble affinity macroligand of large molecular weight and in an excessive amount specifically binds to the target of interest. In the second step, the complex of the target and the macroligand is recovered as retentate after being separated from impurities in an ultrafiltration process using a membrane which has a molecular weight cutoff value substantially larger than the molecular weights of the impurities but substantially smaller than that of the macroligand (U.S. Pat. No. 4,973,554). Since the affinity binding of the target and the macroligand occurs in solution, separation by the affinity ultrafiltration process is kinetically fast, quantitatively efficient and specific, and less prone to nonspecific binding. This is in contrast to the common complications encountered in the solid phase based separation techniques for assaying transferase activity as discussed herein above. These complications include slow binding kinetics, low binding and separation efficiencies (due to the presence of numerous unaccessible or inactive binding ligands on a solid phase), and irreversible and nonspecific binding backgrounds. Another novel feature of the affinity ultrafiltration separation process is that the target-macroligand complex can be easily and efficiently recovered for further manipulations or analysis due to the absence of association of the complex with any solid phase.

The affinity ultrafiltration separation process is also used for assay purpose. One example is the detection of a nucleic acid target of specific sequence. In this example, the target is first hybridized with an excessive amount of a labeled and single-stranded probe having sufficient complementary bases to the target sequence. The probe is designed to have a molecular weight substantially smaller than that of the target. Thus, the hybridization mixture can be regarded as an affinity binding system containing the free probe of small molecular weight and the target-probe hybrid complex of large molecular weight. This labeled hybrid indicative of the target is detected as the retentate after an ultrafiltration separation process with a membrane which retains the hybrid and passes the unhybridized free probe (U.S. Pat. No. 5,034,314). This hybridization assay method actually makes use of a contained separation system which produces little or no aerosol release and requires no manual manipulations. However, it must be noted that the assay concept is applicable only to a system comprising an unlabeled target and a labeled affinity probe of substantially smaller molecular weight. This is based on the notion that the molecular weight ratio of the target-probe complex to the probe must be substantially larger than 2 for effective ultrafiltration separation of these two components. If the probe had a molecular weight larger than that of the target, the ratio would change to smaller than 2, and therefore predict poor ultrafiltration separation.

There is a clear need to improve the transferase activity assay methods described herein above for better simplicity, reliability and economy. Prior to the present invention, the affinity ultrafiltration process was never conceived as a separation means for assay of a labeled target in a sample containing non-target labeled background. In particular, no one applied the affinity ultrafiltration separation process to develop a simpler, more reliable and more economical method for assaying transferase activity than those described in the prior art herein above.

SUMMARY OF THE INVENTION

The present invention discloses a general method for assaying transferase activity which incorporates an affinity ultrafiltration process as a separation means. The assay protocol begins with an assay reaction of a transferase sample to be assayed with an unlabeled substrate and a labeled substrate having a detector label moiety. The position of the label moiety in the labeled substrate permits that the label moiety is incorporated into the product of the assay reaction. This assay reaction product also possesses a binding site moiety either brought about from the unlabeled substrate or existing as a specific structure of the product itself. Next, a sufficient amount of a soluble macroligand having a molecular weight substantially larger than that of the labeled substrate and at least one recognition site specific to the binding site moiety is in contact with the reaction mixture such that at least a substantial fraction of the product forms a complex with the macroligand. In the third step, the complex mixture of the reaction mixture and the macroligand is subjected to ultrafiltration with a membrane which has a molecular weight cutoff value substantially larger than the molecular weight of the labeled substrate but substantially smaller than that of the macroligand. The retentate is then ultrafiltrated with an appropriate solution to at least substantially wash away the residual of the unreacted labeled substrate. This affinity ultrafiltration process effectively separates the labeled product complex into the retentate and the unreacted labeled substrate into the filtrate. A measurement of the final retentate containing the labeled product complex gives the transferase sample's activity of assay interest.

Specific examples of transferase which can be assayed using the affinity ultrafiltration assay method as disclosed in the present invention include, but are not limited to, protein kinase, farnesyl transferase, thymidine kinase, chloramphenicol acetyltransferase, and neomycin phosphotransferase.

The present invention is also directed to a kit which embodies the affinity ultrafiltration separation process for assaying activity of a transferase sample. An exemplary kit includes a labeled substrate, an unlabeled substrate, a reaction buffer, a macroligand, a plurality of devices for performing the ultrafiltration separation process, and an instructional manual teaching how to perform the assay.

DETAILED DESCRIPTION OF THE INVENTION

A transferase sample to be assayed using the method disclosed in the present invention can be an enzyme preparation in a pure or crude form, or in a form of a mixture with at least one enzyme activity modulating compound being of actual assay interest. The enzyme activity modulating compound refers as to an activator or inhibitor for a transferase. In this case, assay for increase or decrease in activity of the transferase is utilized as a means for measuring the potency of the compound in activating or inhibiting the transferase.

A transfer reaction catalyzed by a transferase is in essence a combination process which forms a product by merging one group from one substrate into another group from another substrate. The method for assaying activity of a transferase sample as disclosed in the present invention capitalizes on the strategies for labeling, tagging, affinity separation, recovery, and measurement of the product of the transferase reaction.

Briefly, the present invention relates to a method for assaying transferase activity which comprises the following five key elements in sequence: (1) reacting a transferase sample to be assayed with a labeled substrate and an unlabeled substrate to yield a product having a label moiety from the labeled substrate and a binding site moiety either from the unlabeled substrate or existing as a specific structure of the product, (2) contacting the reaction mixture with a soluble macroligand specific to the binding site moiety such that at least a substantial fraction of the product forms a complex with the macroligand, (3) separating the product-macroligand complex from the unreacted labeled substrate by ultrafiltrating the complex mixture with a membrane which retains the complex and passes the unreacted labeled substrate, (4) washing the retentate, and (5) determining the final retentate.

In comparison to the prior art of the ultrafiltration separation assay for nucleic acid target (U.S. Pat. No. 5,034,314), the concept of this invention differs in that the target to be assayed (the product of the transferase reaction) is in a labeled form in the presence of the labeled background (the unreacted labeled substrate), and is affinity bound by the unlabeled probe of larger molecular weight (the macroligand). This is a logical design for effective ultrafiltration separation of the product label from the unreacted substrate label for the assay purpose because it produces a large molecular weight ratio of the labeled product-macroligand complex to the unreacted labeled substrate. The molecular weight ratio and therefore the ultrafiltration separation effectiveness would be reduced if the macroligand had a molecular weight smaller than those of the labeled product and the labeled substrate.

The method for assaying transferase activity which embodies the present invention is further dissected and discussed in the following sections in sequence.

Assay Reaction for Product Labeling and Tagging

Assay reaction in the present invention generally denotes a reaction of a transferase sample to be assayed with an appropriate substrate and buffer system which can be exploited for measurement of the transferase activity. More specifically, the purpose of this assay reaction is for obtaining a product which can be affinity separated and be measured. To this end, under appropriate conditions an assay reaction of the transferase sample with a labeled substrate and an unlabeled substrate is performed such that a sufficient amount of a product bearing a label moiety and a binding site moiety is yielded. In any case, the binding site moiety is absent from the labeled substrate such that the labeled product can be separated from the unreacted labeled substrate by virtue of the binding site moiety.

Label Moiety and Product Labeling

The terms of label moiety in the present invention refers to a chemical group which can provide a detectable signal. Since most native substrates for transferases contain no readily measurable groups, exogenously introduced label moieties in these substrates (and therefore their products) are usually necessary for any measurements to be made. Specific examples of commonly used labels include, but are not limited to, radioactive isotopes such as $^{32}P$, $^{33}P$, $^{3}H$, $^{14}C$, and $^{35}S$, and nonradioactive fluorescent dyes such as dansyl, coumarin, fluorescein, rhodamine, sulforhodamine, and lissamine rhodamine.

The conventional chemistries for labeling a substrate compound, either radioactively or nonradioactively, are well known to those skilled in the art. Many labeled substrates for assaying activities of the common transferases are also commercially available, some of which are shown in the assay kits and the assay examples described herein below. Often, in the case of the radioactive labeling, the labeled substrate's reactivity toward its transferase to be assayed is not altered to an appreciable extent by the isotopic substitution. The nonradioactive labeling, however, does introduce an exogenous chemical group to the otherwise native substrate. Therefore, the position and chemistry for attaching such nonradioactive label moiety to the substrate is designed in such way that the label moiety does not unacceptably affect the substrate's reactivity toward its transferase to be assayed.

Incorporation of a label moiety into the product of the transferase assay reaction is generally achieved by use of a labeled substrate which contains the label moiety located within the group to be incorporated into the product upon the action of the transferase. This labeled substrate is one of the two substrates required for the assay reaction for a transferase sample.

Binding Site Moiety and Product Tagging

Binding site moiety is a chemical tag present in the product of the transferase assay reaction but absent from the labeled substrate as described herein above. Such chemical tag is required for effecting the product separation by the affinity ultrafiltration process as further discussed herein below. There are two mechanisms by which a binding site moiety can be introduced into the product of the transferase assay reaction.

The first mechanism for having a binding site moiety in the product relies on use of an unlabeled substrate, which together with the labeled substrate as described herein above provides a complete pair of substrates for the transferase assay reaction. This unlabeled substrate contains the binding site moiety located within the group to be incorporated into the product upon the action of the transferase. The binding site moiety can be a native structure of the unlabeled substrate. One example of this kind of binding site moiety is a specific structure in an unlabeled substrate which is recognized and bound by an antibody. Another example is gamma phosphate group of ATP as an unlabeled substrate in a kinase assay reaction which is recognized and bound by a cationic polymer such as soluble diethylaminoethyl dextran. Alternatively, the binding site moiety can be exogenously introduced into the unlabeled substrate using the conventional chemistries well known to those skilled in the art. In principle, the position and chemistry for introducing such exogenous binding site moiety into the unlabeled substrate must meet the requirement that the presence of this moiety does not alter the substrate's reactivity toward its transferase to be assayed to an unacceptable extent. Specific examples of commonly employed exogenous binding site moieties include, but are not limited to, biotin, fluorescein, dinitrophenol, and digoxigenin, all of which are recognized and bound by their respective protein or antibody binders. After the transferase assay reaction, the binding site moiety as either native or exogenous part of the unlabeled substrate is incorporated into the reaction product. It should be noted that this type of binding site moiety exists in the unlabeled substrate, or in both of the product and the unreacted unlabeled substrate of the transferase assay reaction.

The second mechanism for having a binding site moiety in the product takes advantage of the product's distinct structure as a binding site moiety. One example is the specific structure of a phosphorylated peptide product of a protein kinase assay reaction being a binding site moiety as it could be recognized and bound by an antibody. This kind of binding site moiety is present in the product only, and is absent from both of the labeled substrate and the unlabeled substrate.

Post-Reaction Treatment

The transferase assay reaction does not need to be terminated if one of the following four circumstances is met: (1) a qualitative yes-or-no answer about the activity of the transferase sample being assayed is sufficient; (2) the activity of the transferase sample is so high that the assay reaction reaches its maximal extent with at least one of the two substrates depleted; (3) the transferase sample is so unstable or inhibited that the assay reaction itself is terminated at some point during the course of observation; and (4) the assay reaction in progress can be at least substantially terminated upon the subsequent addition of the macroligand solution as discussed herein below. Under any of these circumstances, the assay reaction mixture can be directly used for the subsequent process for product separation.

It is often desirable to better control the uniformity of the assay reaction extent for higher assay reproducibility. This is usually accomplished by terminating the assay reaction in progress prior to the subsequent product separation process so that any post-reaction variability does not affect the assay result. Such termination is commonly employed in quantitative assay which is expected to distinguish different levels of transferase activity. To obtain a dynamic correlation between the transferase activity being assayed and the amount of the product formed, the assay reaction in progress is preferably terminated before it reaches its maximal extent with at least one of the two substrates depleted. Further, the time point at which the assay reaction is terminated is determined by the need of acquiring a sufficient amount of the product for reproducible assay result and the procedural convenience. Still further, the assay reaction is preferably terminated by heating or a stop reagent, which either inactivates or inhibits the transferase in reaction. If the stop reagent is used, it must be compatible with the macroligand which is subsequently added for the affinity ultrafiltration separation process as described herein below. In other words, the presence of the stop reagent in the terminated reaction mixture must not prevent the macroligand from binding to the binding site moiety in the product. If the stop reagent is too harsh, the terminated reaction mixture may need to be properly conditioned with another reagent prior to the macroligand addition.

After the post-reaction treatment, the transferase assay reaction mixture containing the labeled and tagged product, the unreacted labeled substrate and the unreacted unlabeled substrate is ready for the affinity ultrafiltration separation process as described herein below.

Affinity Ultrafiltration for Product Separation

This product separation after the transferase assay reaction is required for determination of the product label upon removal of the interference of the unreacted substrate label. To this end, an affinity ultrafiltration separation process is performed which passes the unreacted labeled substrate but retains the labeled product in complex with a macroligand having at least one recognition site specific to the binding site moiety of the product.

Macroligand and Affinity Binding

Macroligand in the present invention refers to a soluble substance having at least the following three characteristics: (1) a carrier having at least one recognition site which binds with a reasonable affinity and specificity to the binding site moiety of the product formed in the transferase assay reaction, (2) a macromolecule with a molecular weight substantially larger than that of the labeled substrate, and (3) a molecule at least substantially incapable of binding to the labeled substrate nonspecifically.

Under appropriate binding conditions, a sufficient amount of the macroligand in solution is added to and then incubated with the transferase assay reaction mixture such that at least a substantial fraction of the product forms a complex with the macroligand. If this macroligand addition also functions to terminate the assay reaction, it must be controlled in a manner identical to that for terminating the assay reaction as discussed herein above. Preferably, the macroligand is added in excess to complex with all the product and to eliminate the effect of any error in adding the macroligand. When the binding site moiety exists in both of the product and the unreacted unlabeled substrate, the macroligand is preferably added in such an amount that the total recognition sites of the macroligand are equal to or more than the total number of the binding site moiety in the assay reaction. However, if the macroligand binds to the binding site moieties in the product and the unreacted unlabeled substrate equally well, it can also be added in a limited amount. In this case, the product competes with the unreacted unlabeled substrate for binding to the limited recognition sites of the macroligand, forming the product-macroligand complex in an amount in proportion to the product amount produced in the assay reaction. Thus, upon the subsequent separation and measurement, the limited complex can proportionally indicate the transferase activity being assayed. One advantage of such limited macroligand approach is the saving of the macroligand to be used for the transferase activity assay.

The reason for having the product of the transferase assay reaction bound with the macroligand relates to the need of increasing the product's apparent molecular weight for the ultrafiltration separation from the labeled substrate as described herein below. This macroligand affinity binding approach is essential when the product and the labeled substrate both have a molecular weight smaller than about 5,000 daltons which makes ultrafiltration separation of these two components difficult or impossible. Further, the affinity binding between the product and the macroligand in solution is kinetically fast, quantitatively efficient and specific, and relatively free of the nonspecific binding background from the labeled substrate.

Some macroligands have one or a few recognition sites per molecule (e.g. streptavidin or avidin, and antibody), while other macroligands have numerous recognition sites per molecule (e.g. soluble diethylaminoethyl dextran). Specific examples of commonly used macroligands are listed along with their respective binding site moieties as follows:

| Macroligand | Binding Site Moiety |
|---|---|
| Streptavidin or Avidin | Biotin |
| Antibody | |
| Anti-Fluorescein | Fluorescein |
| Anti-Dinitrophenol | Dinitrophenol |
| Anti-Digoxigenin | Digoxigenin |
| Anti-Peptide | Peptide |
| Anti-Phosphorylated Peptide | Phosphorylated Peptide |
| Soluble Diethylaminoethyl Dextran | Phosphate |

Ultrafiltration Separation

At last, separation of the labeled product from the unreacted labeled substrate is completed in an ultrafiltration process engaging the complex sample comprising the assay reaction mixture and the macroligand. The ultrafiltration membrane used herein is chosen to have a molecular weight cutoff value substantially larger than the molecular weight of the labeled substrate but substantially smaller than that of the macroligand. Such ultrafiltration process effectively separates the labeled product-macroligand complex into the retentate and the unreacted labeled substrate into the filtrate. In addition to the initial step of ultrafiltrating the complex sample, several steps of ultrafiltration washing with at least one appropriate solution are generally required. These washing steps serve to at least substantially remove the nonspecific retention and adsorption of the unreacted labeled substrate from the retentate in the ultrafiltration system. These washing steps are still required even if the transferase activity being assayed is so high that all the labeled substrate is converted to the product with no unreacted labeled substrate left. In this case, the washing steps are literally needed to demonstrate the high activity by showing all the label in the retentate and no label in the filtrate after the washing steps. Further, the washing solution used must not disrupt the product-macroligand complex, and must not cause the labeled substrate to aggregate in or nonspecifically absorb to the ultrafiltration system.

The ultrafiltration separation process can generally be carried out in a contained system which is relatively free of aerosol release and manual manipulations (U.S. Pat. No. 4,973,554 and U.S. Pat. No. 5,034,314). This contained separation system is operationally simple, and particularly desirable when a radioactive sample is processed. Several commercial vendors, including Amicon (Beverly, Mass.) and Nalgene (Rochester, N.Y.), offer a microdevice for conducting a microcentrifuge based process of ultrafiltration separation with a range of selections in molecular weight cutoff (Amicon® Technical Bulletin, Microcon® Microconcentrators, 1996). This kind of compact and contained centrifugal device makes an ultrafiltration separation process for small assay volume (usually from about 5 µL to about 1000 µL) particularly fast, easy and convenient to perform. Also, multiple samples can be simultaneously processed in the microcentrifugal process of ultrafiltration separation, yielding a higher throughput than that achievable with other separation techniques requiring manual manipulations of individual samples. If the inherently efficient affinity ultrafiltration process performed in such compact and contained device is utilized as a separation means for assaying transferase activity, the reagents used and the waste generated in the assay process can be substantially minimized. This is an advantage particularly desirable when a radioactive reagent is used for assaying transferase activity. Further, it is very easy and convenient to recover the retentate in the microdevice for analysis or detection with an invert spin. Therefore the centrifugal ultrafiltration microdevice is clearly a suitable and preferred platform for performing the affinity ultrafiltration separation process as required in the transferase activity assay method disclosed in the present invention.

Separation by the affinity ultrafiltration process as described herein above offers not only low nonspecific background, but also high reproducibility. This combination of low nonspecific background and high reproducibility produces high sensitivity for transferase activity assay utilizing the affinity ultrafiltration separation process. Further, the streamlined process of the affinity ultrafiltration separation is achieved with the readily available and conventional reagents, chemistries, and devices, and therefore produces an assay economy of low cost and high throughput if it is used for assaying transferase activity.

Therefore, upon the affinity ultrafiltration spearation for the assay reaction mixture, the product label and the unreacted substrate label are respectively separated into the retentate and the filtrate. The final retentate containing the separated product label, which is at least substantially free of the unreacted substrate label, is ready for the recovery and measurement as described herein below.

Product Recovery and Measurement

This product recovery and measurement after the affinity ultrafiltration separation process is simply for the purpose of indicating the activity of the transferase sample being assayed. Again, the affinity ultrafiltration separation system itself provides a simple and contained means to recover the separated product in the form of the final retentate without the risk of aerosol release and the need of inconvenient manual manipulations. The specific manner to recover and measure the final retentate is largely dependent on the label used.

When the centrifugal ultrafiltration microdevice described herein above is used, the retentate of a radioactively labeled product-macroligand complex can be recovered together with the whole sample holder, which as part of the microdevice contains the ultrafiltration membrane and the retentate. As an alternative, the radioactive retentate can be recovered as a liquid solution through an invert spin (Amicon® Technical Bulletin, Microcon® Microconcentrators, 1996). This invert spin technique usually recovers most of the retentate, which by mechanism does not bind to the ultrafiltration system. These two types of recovered radioactive retentate sample can be counted by use of one of conventional radioactive counting methods. However, the counting with the retentate sample recovered by the invert spin technique tends to be more efficient and reproducible than that with the retentate sample recovered with the whole sample holder, particularly when one of the low-energy labels such as $^3$H, $^{14}$C, $^{35}$S, and $^{33}$P is used. If a liquid scintillation technique is used to count the recovered retentate samples, the liquid scintillation cocktail is added in excess relative to the retentate sample volume so that the counting variability caused by the variable retentate volume can be controlled to a negligible level. The preferred volume ratio of the liquid scintillation cocktail to the retentate sample liquid is larger than 10.

When a nonradioactive label is used, direct detection of such label in the whole sample holder of the centrifugal ultrafiltration microdevice is usually difficult or impossible. Therefore the nonradioactive retentate is preferably recovered using the invert spin technique for the ease of detection. Again, the recovered retentate is sufficiently diluted, preferably at larger than a 1:10 dilution factor, with an appropriate solution prior to the detection so that the effect of the variable retentate volume on the detection result can be kept minimal.

Transferase Activity Assay Kits

To embody and utilize the scope and spirit of the present invention, a kit is assembled which functions as a system comprising the necessary components for performing the affinity ultrafiltration assay for transferase activity as described herein above. A basic kit for quantifying activity of a transferase sample comprises at least a labeled substrate and an unlabeled substrate. These two substrates are active and specific to the transferase to be assayed and, upon the action of the transferase under appropriate conditions, jointly yield a product having a label moiety from the labeled substrate and a binding site moiety either from the unlabeled substrate or existing as a specific structure of the product. The kit could further comprise one or more of the following three items: (1) a reaction buffer for effecting an assay reaction of the transferase sample to be assayed with the labeled substrate and the unlabeled substrate, (2) a soluble macroligand which has a molecular weight substantially larger than that of the labeled substrate and at least one recognition site specific to the binding site moiety of the product, and (3) a plurality of devices for performing the ultrafiltration separation process which contain a membrane having a molecular weight cutoff value substantially larger than the molecular weight of the labeled substrate but substantially smaller than that of the macroligand. An instructional manual teaching how to perform the assay could also be included in the kit.

Each of the exemplary assay kits described herein below further specifies the core components for performing the affinity ultrafiltration assay for the specific type of transferase activity. It is obvious that these components in each assay system can be packed into several suitable containers, along with an instructional manual, to assemble the specific type of kit. In any case, these kits are intended to illustrate more fully the concept and nature of the present invention without acting as a limitation upon its scope and spirit.

Protein Kinase Assay Kit No. 1: gamma $^{32}$P-ATP (labeled substrate), a peptide containing at least one tyrosine, serine, threonine or histidine residue which can be phosphorylated by a protein kinase, and a biotin tag attached to the carboxy or amino terminus (unlabeled substrate), streptavidin or avidin (macroligand), and a centrifugal ultrafiltration microdevice with a membrane having a molecular weight cutoff value substantially larger than the molecular weight of gamma $^{32}$P-ATP but substantially smaller than that of streptavidin or avidin (ultrafiltration separation).

Protein Kinase Assay Kit No. 2: gamma $^{32}$P-ATP (labeled substrate), a peptide containing at least one tyrosine, serine, threonine or histidine residue which can be phosphorylated by a protein kinase (unlabeled substrate), an antibody specific to both of the native peptide substrate and the phosphorylated peptide product (macroligand), and a centrifugal ultrafiltration microdevice with a membrane having a molecular weight cutoff value substantially larger than the molecular weight of gamma $^{32}$P-ATP but substantially smaller than that of the antibody (ultrafiltration separation).

Protein Kinase Assay Kit No. 3: gamma $^{32}$P-ATP (labeled substrate), a peptide containing at least one tyrosine, serine, threonine or histidine residue which can be phosphorylated by a protein kinase (unlabeled substrate), an antibody specific to the phosphorylated peptide product (macroligand), and a centrifugal ultrafiltration microdevice with a membrane having a molecular weight cutoff value substantially larger than the molecular weight of gamma $^{32}$P-ATP but substantially smaller than that of the antibody (ultrafiltration separation).

Protein Kinase Assay Kit No. 4: a peptide containing at least one tyrosine, serine, threonine or histidine residue which can be phosphorylated by a protein kinase, and a label selected from the group consisting of $^3$H, $^{14}$C and a fluorescent dye attached to the carboxy or amino terminus (labeled substrate), ATP (unlabeled substrate), an antibody specific to the phosphorylated peptide product (macroligand), and a centrifugal ultrafiltration microdevice with a membrane having a molecular weight cutoff value substantially larger than the molecular weight of the labeled peptide substrate but substantially smaller than that of the antibody (ultrafiltration separation).

Farnesyl Transferase Assay Kit No. 1: $^3$H or $^{14}$C labeled FPP (labeled substrate), a peptide containing a cysteine residue which can be farnesylated by a farnesyl transferase, and a biotin tag attached to the carboxy or amino terminus (unlabeled substrate), streptavidin or avidin (macroligand), and a centrifugal ultrafiltration microdevice with a membrane having a molecular weight cutoff value substantially larger than the molecular weight of the labeled FPP but substantially smaller than that of streptavidin or avidin (ultrafiltration separation).

Farnesyl Transferase Assay Kit No. 2: $^3$H or $^{14}$C labeled FPP (labeled substrate), a peptide containing a cysteine residue which can be farnesylated by a farnesyl transferase (unlabeled substrate), an antibody specific to both of the native peptide substrate and the farnesylated peptide product (macroligand), and a centrifugal ultrafiltration microdevice with a membrane having a molecular weight cutoff value substantially larger than the molecular weight of the labeled FPP bur substantially smaller than that of the antibody (ultrafiltration separation).

Thymidine Kinase Assay Kit No. 1: $^3$H-thymidine (labeled substrate), ATP (unlabeled substrate), a soluble diethylaminoethyl dextran of molecular weight of about 100,000 daltons to about 1,000,000 daltons (macroligand), and a centrifugal ultrafiltration microdevice with a membrane having a molecular weight cutoff value substantially larger than the molecular weight of $^3$H-thymidine but substantially smaller than that of the diethylaminoethyl dextran (ultrafiltration separation).

Thymidine Kinase Assay Kit No. 2: gamma $^{32}$P-ATP (labeled substrate), thymidine containing a biotin tag attached to a position without unacceptably affecting the substrate's reactivity toward the kinase (unlabeled substrate), streptavidin or avidin (macroligand), and a centrifugal ultrafiltration microdevice with a membrane having a molecular weight cutoff value substantially larger than the molecular weight of gamma $^{32}$P-ATP but substantially smaller than that of streptavidin or avidin (ultrafiltration separation).

Chloramphenicol Acetyltransferase Assay Kit: $^3$H or $^{14}$C labeled acetyl CoA (labeled substrate), chloramphenicol containing a biotin tag attached to a position without unacceptably affecting the substrate's reactivity toward the transferase (unlabeled substrate), streptavidin or avidin (macroligand), and a centrifugal ultrafiltration microdevice with a membrane having a molecular weight cutoff value substantially larger than the molecular weight of the labeled acetyl CoA but substantially smaller than that of streptavidin or avidin (ultrafiltration separation).

Neomycin Phosphotransferase Assay Kit: gamma $^{32}$P-ATP (labeled substrate), neomycin containing a biotin tag attached to a position without unacceptably affecting the substrate's reactivity toward the transferase (unlabeled substrate), streptavidin or avidin (macroligand), and a centrifugal ultrafiltration microdevice with a membrane having a molecular weight cutoff value substantially larger than the molecular weight of gamma $^{32}$P-ATP but substantially smaller than that of streptavidin or avidin (ultrafiltration separation).

Assay Examples

The specific assay examples described herein below further illustrate in operational details the affinity ultrafiltration separation method for assaying transferase activity as disclosed in the present invention. Again, these examples are not intended in any way to otherwise limit the scope and spirit of the disclosure or protection granted by the patent.

It should be noted that the assay examples share a common affinity ultrafiltration separation system. This system comprises biotin as an exogenous binding site moiety in all the unlabeled substrates, streptavidin or avidin as a macroligand, and the centrifugal ultrafiltration microdevice with a membrane having a molecular weight cutoff value from about 30,000 daltons to about 50,000 daltons as an ultrafiltration platform. This affinity ultrafiltration separation system is preferred for assaying transferase activity for at least the following six reasons: (1) this single separation system can be implemented to many assay systems for different types of transferase activity; (2) attachment of a biotin tag to an unlabeled substrate can usually be done using well-established chemistries without significantly affecting the substrate's reactivity toward its transferase to be assayed because of the small size of biotin; (3) the affinity binding between biotin and streptavidin or avidin has been well characterized; (4) highly purified biotin, streptavidin, and avidin are readily available commercially; (5) the binding between biotin and streptavidin or avidin is very stable, reliable and consistent under most assay conditions as it has the highest affinity among known small ligand-protein binding systems and the exceptional resistance to a variety of denaturing conditions; and (6) the molecular weight cutoff value of the centrifugal ultrafiltration microdevice corresponds to a dynamic membrane structure which produces the highest flow rate of ultrafiltration under most operational conditions (Amicon® Technical Bulletin, Microcon® Microconcentrators, 1996).

The following reagents and materials are commonly used in all the three assay examples described herein below. They are commercially available from their respective vendors: streptavidin or avidin (M.W. about 60,000 daltons), Sigma (St. Louis, Mo.); Microcon-50 (M.W. cutoff 50,000 daltons) or Microcon-30 (M.W. cutoff 30,000 daltons) centrifugal ultrafiltration microdevice, Amicon; and Ready Safe™ liquid scintillation cocktail, Beckman (Fullerton, Calif.).

EXAMPLE 1

Protein Tyrosine Kinase Assay

EGF receptor (a protein tyrosine kinase), biotinylated PTK peptide, and 5x PTK assay buffer are commercially available from Promega (Madison, Wis.); gamma $^{32}$P-ATP from Amersham (Arlington Heights, Ill.).

An assay reaction is initiated by adding 5 µL of EGF receptor to a mixture of 25 µM gamma $^{32}$P-ATP (0.02 µCi/µL), 0.3 mM biotinylated PTK peptide, 0.1 mM sodium vanadate in 20 µL of 1x PTK assay buffer in an appropriate container tube. A control reaction with 5 µL of water in place of EGF receptor is also constructed. After an incubation of 15 minutes at 30° C., the assay and control reactions are both terminated by addition of 12.5 µL of 7.5M guanidine hydrochloride solution.

To the terminated reaction mixtures are added 50 µL of 2 mg/mL streptavidin solution. After an incubation of 5 minutes at room temperature, the assay and control samples are each loaded into a Microcon-50 centrifugal ultrafiltration microdevice. A spin of 5 minutes at 14,000×g in a microcentrifuge removes most of the samples' liquid into the filtrate. To the ultrafiltration devices are added 100 µL of 0.5M $Na_2HPO_4$ solution followed by another spin of 5 minutes at 14,000×g. This wash step is repeated twice. Finally the retentates are each recovered into a clean container tube by an invert spin of the ultrafiltration devices for 30 seconds at 14,000×g. The recovered samples are each placed in a liquid scintillation vial followed by addition of 10 mL of Ready Safe™ liquid scintillation cocktail. These vials are then counted using a conventional liquid scintillation counter with a channel set for $^{32}$P. The net count of the assay sample minus the control sample represents the activity of the EGF receptor sample being assayed. Additional wash steps may be tried if the background count of the control sample is too high compared to that of the assay sample.

EXAMPLE 2

Farnesyl Transferase Assay

Farnesyl transferase, $^3$H-FPP, biotinylated FT peptide substrate, and FT assay buffer are commercially available from Amersham.

An assay reaction is initiated by adding 5 µL of farnesyl transferase sample at an appropriate activity concentration to a mixture of 0.4 µM $^3$H-FPP (0.01 µCi/µL), 4 µM biotinylated FT peptide in 20 µL of 1x FT assay buffer in an appropriate container tube. A control reaction with 5 µL of water in place of the enzyme sample is also constructed. After an incubation of 60 minutes at 37° C., the assay and control reactions are both terminated by addition of 200 µL of 20 mM Tris-chloride (pH 7.5) buffer containing 0.5 mg/mL bovine serum albumin, 2% sodium lauryl sulfate, and 0.5M NaCl.

To the terminated reaction mixtures are added 5 µL of 2 mg/mL streptavidin solution. After an incubation of 5 minutes at room temperature, the assay and control samples are each loaded into a Microcon-50 centrifugal ultrafiltration microdevice. A spin of 5 minutes at 14,000×g in a microcentrifuge removes most of the samples' liquid into the filtrate. To the ultrafiltration devices are added 100 µL of 20 mM Tris-chloride (pH 7.5) buffer containing 1% sodium lauryl sulfate, and 150 mM NaCl followed by another spin of 5 minutes at 14,000×g. This wash step is repeated twice. Finally the retentates are each recovered into a clean container tube by an invert spin of the ultrafiltration devices for 30 seconds at 14,000×g. The recovered samples are each placed in a liquid scintillation vial followed by addition of 10 mL of Ready Safe™ liquid scintillation cocktail. These vials are then counted using a conventional liquid scintillation counter with a channel set for $^3$H. The net count of the assay sample minus the control sample represents the activity of the farnesyl transferase sample being assayed. Additional wash steps may be tried if the background count of the control sample is too high compared to that of the assay sample.

EXAMPLE 3

Chloramphenicol Acetyltransferase Assay

Chloramphenicol acetyltransferase, $^3$H-acetyl CoA, biotinylated chloramphenicol, and CAT assay buffer are commercially available from NEN™ Life Science Products (Boston, Mass.).

An assay reaction is initiated by adding 5 µL of chloramphenicol acetyltransferase sample at an appropriate activity concentration to a mixture of 90 µM $^3$H-acetyl CoA (1 nCi/µL), 0.2 mM biotinylated chloramphenicol in 20 µL of 1x CAT assay buffer in an appropriate container tube. A control reaction with 5 µL of water in place of the enzyme sample is also constructed. After an incubation of 60 minutes at 37° C., the assay and control reactions are both terminated by addition of 200 µL of 20 mM Tris-chloride (pH 8.0) buffer containing 2% sodium lauryl sulfate, and 0.5M NaCl.

To the terminated reaction mixtures are added 50 µL of 2 mg/mL streptavidin solution. After an incubation of 5 minutes at room temperature, the assay and control samples are each loaded into a Microcon-50 centrifugal ultrafiltration microdevice. A spin of 5 minutes at 14,000×g in a microcentrifuge removes most of the samples' liquid into the filtrate. To the ultrafiltration devices are added 100 µL of 20 mM Tris-chloride (pH 8.0) buffer containing 1% sodium lauryl sulfate, and 150 mM NaCl followed by another spin of 5 minutes at 14,000×g. This wash step is repeated twice. Finally the retentates are each recovered into a clean container tube by an invert spin of the ultrafiltration devices for 30 seconds at 14,000×g. The recovered samples are each placed in a liquid scintillation vial followed by addition of 10 mL of Ready Safe™ liquid scintillation cocktail. These vials are then counted using a conventional liquid scintillation counter with a channel set for $^3$H. The net count of the assay sample minus the control sample represents the activity of the chloramphenicol acetyltransferase sample being assayed. Additional wash steps may be tried if the background count of the control sample is too high compared to that of the assay sample.

Conclusion

Accordingly, in comparison to the prior art, assay of transferase activity incorporating the affinity ultrafiltration separation process as disclosed in the present invention can be performed easily and conveniently while achieving high reliability and throughput. The affinity ultrafiltration process is applied to this invention to separate the labeled product from the unreacted labeled substrate in the transferase assay reaction mixture. This application overcomes many problems associated with the solid phase based separation techniques as commonly encountered in the prior art concerning transferase activity assay. These problems include slow binding kinetics, low binding and separation efficiencies (due to the presence of a large number of unaccessible or inactive binding ligands on a solid phase), and irreversible and nonspecific binding backgrounds. In particular, the affinity ultrafiltration separation process for assaying transferase activity as disclosed in the present invention offers the distinct advantages in that it facilitates ultrafiltration separation of the transferase assay reaction mixture containing the small molecules of the labeled product and the unreacted labeled substrate by selectively complexing the product with a macroligand of substantially larger molecular weight;

it provides a mechanism of solution phase affinity binding which results in affinity separation characterized by fast binding kinetics, quantitative efficiency and specificity, and low non-target (the labeled substrate) background;

it provides a contained separation system which significantly streamlines the handling by eliminating manual manipulations, and reduces the risk of aerosol spillage particularly when a radioactive reagent is used;

it provides a contained, compact and efficient separation system which significantly reduces the reagents used, and the radioactive waste generated when a radioactive label is used;

it provides a simple means to collect or recover the separation product for detection;

it provides high assay sensitivity as the separation process has low nonspecific background and high reproducibility; and it realizes an assay economy by streamlining the assay operations, increasing the assay throughput, and using the readily available and conventional reagents, chemistries, and devices.

Although the description herein above contains many specificities, these merely provide illustrations of some of the presently preferred embodiments of the present invention with no intention to limit the scope and spirit of the invention. For example, transferase which can be assayed using the affinity ultrafiltration separation technique as disclosed in this invention can be extended to DNA or RNA polymerase, terminal deoxynucleotidyl transferase, polynucleotide kinase, DNA or RNA ligase, glycosyltransferase, etc.; the centrifugal device for the affinity ultrafiltration separation process described herein above can be substituted by a pressure system.

Thus the scope and spirit of the present invention should be determined by the appended claims and their legal equivalents, rather than by the examples given.

What is claimed is:

1. A method for assaying activity of a transferase comprising the steps of: (1) under appropriate conditions which render said transferase active reacting said transferase with a labeled substrate and an unlabeled substrate to yield a product having a label moiety from said labeled substrate and a binding site moiety either from said unlabeled substrate or existing as a specific structure of said product, (2) contacting the reaction mixture with a sufficient amount of a solution of a macroligand having a molecular weight substantially larger than that of said labeled substrate and at least one recognition site specific to said binding site moiety such that at least a substantial fraction of said product forms a complex with said macroligand, (3) subjecting the complex mixture to ultrafiltration with a membrane having a molecular weight cutoff value substantially larger than the molecular weight of said labeled substrate to pass the unreacted labeled substrate but substantially smaller than that of macroligand to retain said complex, (4) washing the retentate containing said complex by said ultrafiltration with an appropriate solution to at least substantially remove the residual of said unreacted labeled substrate from said retentate, and (5) by means of said label moiety determining the final retentate containing the separated product at least substantially free of said unreacted labeled substrate as a measure of said activity of said transferase.

2. The method of claim 1 wherein said ultrafiltration is effected using centrifugal force with a centrifugal ultrafiltration device.

3. The method of claim 2 further comprising between step (4) and step (5) the step of recovering said final retentate by invert centrifugation of said centrifugal ultrafiltration device.

4. The method of claim 1 wherein said transferase is selected from the group consisting of protein kinase, farnesyl transferase, thymidine kinase, chloramphenicol acetyltransferase and neomycin phosphotransferase.

5. The method of claim 1 wherein said binding site moiety is an exogenous biotin tag which is present in the part of said unlabeled substrate to be incorporated into said product upon the action of said transferase and wherein said macroligand is selected from the group consisting of streptavidin and avidin.

6. The method of claim 5 wherein said ultrafiltration is effected using centrifugal force with a centrifugal ultrafiltration device and wherein said membrane has a molecular weight cutoff value from about 30,000 daltons to about 50,000 daltons.

7. The method of claim 6 further comprising between step (4) and step (5) the step of recovering said final retentate by invert centrifugation of said centrifugal ultrafiltration device.

8. The method of claim 6 further comprising between step (1) and step (2) the step of terminating the reaction in progress before at least one member selected from the group consisting of said labeled substrate and said unlabeled substrate becomes depleted.

9. The method of claim 6 wherein said transferase is a protein kinase.

10. The method of claim 9 wherein said labeled substrate is gamma $^{32}$P-ATP and wherein said unlabeled substrate is a peptide having said exogenous biotin tag attached to a position selected from the group consisting of the carboxy terminus and the amino terminus.

11. The method of claim 10 wherein said protein kinase exists in a form selected from the group consisting of a purified preparation, a crude preparation and a mixture with a protein kinase activity modulating compound of actual assay interest.

12. The method of claim 6 wherein said transferase is a farnesyl transferase.

13. The method of claim 12 wherein said labeled substrate is selected from the group consisting of $^3$H-FPP and $^{14}$C-FPP and wherein said unlabeled substrate is a peptide having said exogenous biotin tag attached to a position selected from the group consisting of the carboxy terminus and the amino terminus.

14. The method of claim 13 wherein said farnesyl transferase exists in a form selected from the group consisting of a purified preparation, a crude preparation and a mixture with a farnesyl transferase activity modulating compound of actual assay interest.

15. The method of claim 6 wherein said transferase is a chloramphenicol acetyltransferase.

16. The method of claim 15 wherein said labeled substrate is selected from the group consisting of $^3$H-acetyl CoA and $^{14}$C-acetyl CoA and wherein said unlabeled substrate is biotinylated chloramphenicol.

17. The method of claim 16 wherein said chloramphenicol acetyltransferase exists in a form selected from the group consisting a purified preparation and a crude preparation.

18. The method of claim 1 wherein said binding site moiety is an exogenous chemical tag selected from the group consisting of fluorescein, dinitrophenol and digoxigenin which is present in the part of said unlabeled substrate to be incorporated into said product upon the action of said transferase and wherein said macroligand is an antibody specific to said exogenous chemical tag.

19. A kit for assaying activity of a transferase sample comprising: (1) a radioactive substrate, (2) an unlabeled substrate having an exogenous biotin tag, (3) a reaction buffer for effecting a reaction of said transferase sample with said radioactive substrate and said unlabeled substrate, (4) a macroligand selected from the group consisting of streptavidin and avidin, and (5) a plurality of centrifugal ultrafiltration devices with a membrane having a molecular weight cutoff value from about 30,000 daltons to about 50,000 daltons.

20. The kit of claim 19 wherein said transferase sample is a protein kinase sample.

21. The kit of claim 20 wherein said radioactive substrate is gamma $^{32}$P-ATP and wherein said unlabeled substrate is a peptide having said exogenous biotin tag attached to a position selected from the group consisting of the carboxy terminus and the amino terminus.

22. The kit of claim 21 wherein said protein kinase sample exists in a form selected from the group consisting of a purified preparation, a crude preparation and a mixture with a protein kinase activity modulating compound of actual assay interest.

23. The kit of claim 19 wherein said transferase sample is a farnesyl transferase sample.

24. The kit of claim 23 wherein said radioactive substrate is selected from the group consisting of $^3$H-FPP and $^{14}$C-FPP and wherein said unlabeled substrate is a peptide having said exogenous biotin tag attached to a position selected from the group consisting of the carboxy terminus and the amino terminus.

25. The kit of claim 24 wherein said farnesyl transferase sample exists in a form selected from the group consisting of a purified preparation, a crude preparation and a mixture with a farnesyl transferase activity modulating compound of actual assay interest.

26. The kit of claim 19 wherein said transferase sample is a chloramphenicol acetyltransferase sample.

27. The kit of claim 26 wherein said radioactive substrate is selected from the group consisting of $^3$H-acetyl CoA and $^{14}$C-acetyl CoA and wherein said unlabeled substrate is biotinylated chloramphenicol.

28. The kit of claim 27 wherein said chloramphenicol acetyltransferase sample exists in a form selected from the group consisting of a purified preparation and a crude preparation.

29. A general-purpose kit for assaying activity of a transferase sample comprising: (1) a macroligand selected from the group consisting of streptavidin and avidin, and (2) a plurality of centrifugal ultrafiltration devices with a membrane having a molecular weight cutoff value from about 30,000 daltons to about 50,000 daltons.

* * * * *